United States Patent [19]

Chow et al.

[11] Patent Number: 4,687,776

[45] Date of Patent: Aug. 18, 1987

[54] DRUG STABILIZATION

[75] Inventors: Li Hang Chow, Whippany; Mahdi B. Fawzi, Flanders; Isaac Ghebre-Sellassie, Stanhope, all of N.J.

[73] Assignee: Warner-Lambert Company, Morris Plains, N.J.

[21] Appl. No.: 922,646

[22] Filed: Oct. 24, 1986

[51] Int. Cl.$^4$ ........................................... C07D 215/22
[52] U.S. Cl. .................................. 514/312; 546/157; 436/8
[58] Field of Search ................ 514/312; 544/184, 243; 424/249, 258; 546/157; 436/8-18

[56] References Cited

U.S. PATENT DOCUMENTS 4,278,673 7/1981 Hartley et al. ....................... 514/243
4,579,854 4/1986 Iwakuma et al. .................... 546/157
4,616,022 10/1986 Ghebre-Sellassie et al. ........ 546/157

Primary Examiner—Deborah L. Kyle
Assistant Examiner—T. J. Wallen
Attorney, Agent, or Firm—Sandra M. Person; Ronald A. Daignault

[57] ABSTRACT

Certain derivatives of procaterol are believed to possess similar biological activity to the base compound, (i.e., as bronchodilators) but have greater stability and bioavailability.

4 Claims, No Drawings

DRUG STABILIZATION

BACKGROUND

Procaterol is a 8-hydroxy-5-[1-hydroxy-2-[(1-methyl ethyl)amino]butyl]-2(1H)-quinolinone, monohydrochloride, hemihydrate.

The compound is known to be a bronchodilator, a peripheral vasodilator, and an antihypertensive agent.

THE INVENTION

It has been discovered that the thermal stability, and lipophilicity of procaterol can be enhanced by reacting procaterol, or certain salts thereof, with suitable reagents to produce certain ethers or esters at the phenolic hydroxyl cite of the molecule.

In a preferred embodiment, procaterol hydrochloride was contacted with sodium hydroxide and ethyl bromide in the presence of methanol solvent for several days over moderate heat. After removal of the solvent via evaporation and the separation of unreacted phenol and sodium hydroxide by solvent extraction, 1.5q of 8-ethoxy procaterol was isolated via recrystallization. The reaction scheme is believed to be:

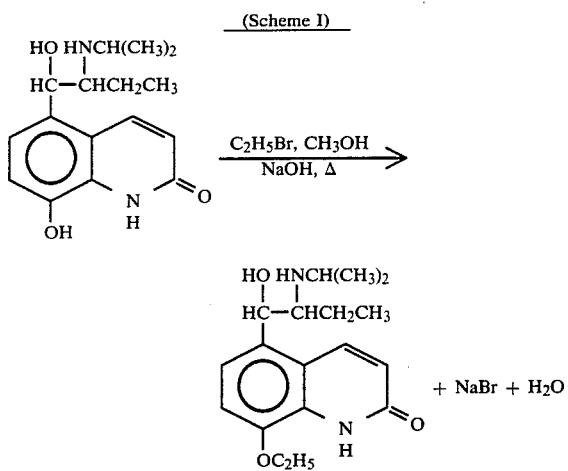

In a similar fashion, esters can be produced via:

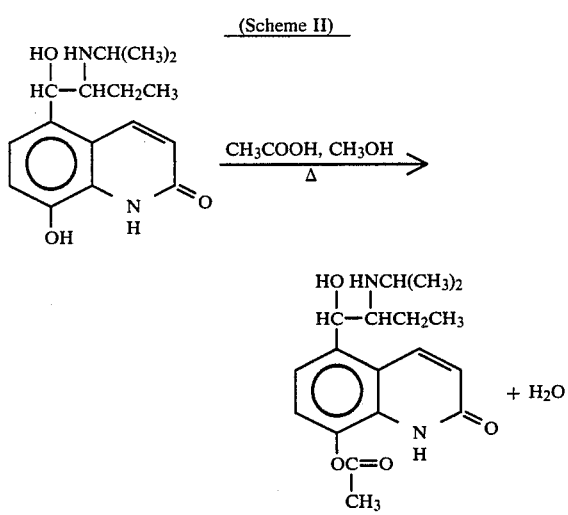

These derivatives may also be prepared from 8-alkyloxy-carbostyril or 8-acyloxy carbostyril as procaterol is synthesized from 8-hydroxycarbostyril.

ADVANTAGES

The process of the invention produces procaterol derivatives which are superior to procaterol and well known salts thereof in several respects. First, the subject ethers and esters are more resistant to heat when in solution. Secondly, because these derivatives are more lipophilic, they should have greater bioavailability when administered via oral or transmembranal routes. These derivatives are expected to have higher octanol/water partition coefficients.

These and other advantages will be more apparent upon consideration of the following description of the invention.

DESCRIPTION OF THE INVENTION

The invention deals with derivatives of procaterol which metabolize into bioavailable form(s) of the drug in the human body.

Principally, the invention is connected with 8-position ether or ester derivatives of procaterol or pharmaceutically acceptable salts thereof. By employing these derivatives in pharmaceutical preparation in place of all or part of the procaterol or procaterol salt, the temperature stability solubility and bioavailability of the drug can be enhanced.

The derivatives of the invention are made by contacting procaterol, or a pharmaceutically acceptable salt thereof, with an acid, halide and/or other suitable reagent which contains the substituent which is ultimately to reside in the 8-position in the resultant ether or ester.

By pharmaceutically acceptable salts, applicants mean any suitable organic or inorganic salt which retains the medicament value of procaterol. Acid addition salts are typical. Exemplary acid salts include hydrochloride, hydrobromide, orthophosphate, benzoate, maleate, tartrate, succinate, citrate, salicylate, sulfate, acetate, and the like.

THE DERIVATIVES

The derivatives of procaterol with which the invention deals are compounds of the following formula:

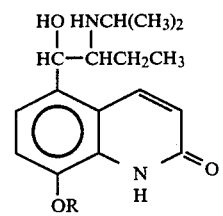

wherein R is a $C_{2-10}$ alkyl, aralkyl, alkaryl, or acyl group.

When R is an alkyl group, it is generally derived from an alkyl halide, e.g., a bromide, or other suitable reagent from which an intact alkyl moiety can be generated in the presence of catalysts or other agents or forces which do not affect the structure of the procaterol base.

Generally, when R is an alkyl group it will contain from 2 to 10 carbon atoms. It may be a branched chain group, but aliphatic groups are preferred. Ethyl, propyl and n-butyl groups are generally preferred. Ethyl is highly preferred.

If R is aralkyl or alkaryl, it generally contains only one aromatic ring. While hetero rings may be present, it is generally preferred that non-heterocyclics be used.

When R is an acyl group it will be one which may be chemically cleaved from a suitable reactant, e.g., an acid or acid halide, via the action of catalysts or other forces or means which do not affect the procaterol structure as such.

Generally, when R is an acyl group it will contain from 2 to 10 carbon atoms. It may contain an aryl moiety. Radicals derived from acetic, propionic, and butyric acids are preferred. The acetic moiety is highly preferred.

While it is generally preferred that the R group contain only carbon, hydrogen and, optionally, oxygen atoms, the presence of non-deleterious moieties is contemplated.

REACTION CONDITIONS

Generally, the derivatives of the invention are produced when suitable reactants are brought together in an environment such that replacement of the hydrogen of the phenolic hydroxyl group of procaterol with alkyl, aralkyl, alkaryl and/or acyl group(s) is facilitated. The parameters under which such reactions occur are generally well known. However, suitable conditions, from which the skilled artisan can extrapolate, are discussed hereinafter.

The temperature at which the reaction takes place will generally be from about 30° C. to about 50° C., preferably about 45° C.

Reaction pressures are not critical. However, typical pressure is under one atm.

The length of reaction will generally be from about 1 to about 5 days, with about 2 days preferred.

Recovery techniques include, but are not limited to, such processes as recrystallization, vacuum separation, solvent extraction, evaporation, and the like. Combinations of one or more of these techniques with other recovery/purification methods are contemplated.

REACTION MEDIUM

The reaction will generally take place in the presence of a acidic or basic environment and a solvent. However, either or both of these features could be eliminated if a general reaction scheme which otherwise compensated for the missing feature(s) were employed.

Useful solvents include, but are not limited to, alcohols, e.g., methanol, ethanol; ethylene glycol, proylene glycol and the like. Methanol is a preferred diluent. Mixtures are operable.

The quantity of acid or base employed is not critical. Generally, a quantity of about 1 wt % to about 5 wt % of basic or alkaline agent and about 0.5 wt % to about 5 wt. % acidic agents will be used for the desired product(s). Weight percentages are based on the weight of all chemical contents of the reaction vessel.

The ether producing agents will generally be one or more alkaline materials for ether products. Suitable materials include NaOH, KOH and the like. NaOH is preferred.

The acidic agent to be used to make esters will generally be a mineral acid, e.g., HCl and the like. HCl is preferred.

Mixtures of the above-mentioned agents can be used.

EXAMPLE 1

8-ethoxyprocaterol was prepared by dissolving 4 grams of procaterol hydrochloride, 1 gram of sodium hydroxide and 4 ml of ethylbromide in 100 ml of methanol and heating the solution at 45° for two days (Scheme I). After evaporation of the solvent and removal of the unreacted procaterol and sodium hydroxide by solvent extraction, 1.5 g of 8-ethoxyprocaterol was isolated by recrystallization from acetone. The reaction takes place as shown in Scheme I, above.

EXAMPLE 2

The enhanced bioavailability and thermal stability of the instant derivatives is demonstrated by the following table:

TABLE

Effect of Light and Heat on the Stability of Procaterol and 8-ethoxyprocaterol in solution.*

| Storage Temperature and Time | Drug Concentration ug/ml | Medium** | % Recovery Procaterol | % Recovery 8-ethoxyprocaterol |
|---|---|---|---|---|
| 45° C. 1 week | 200 | MeOH/H$_2$O(1:1) | — | 100 |
| 45° C. 1 week | 200 | MeOH/0.1 N NaOH(1:1) | — | 98.5 |
| 45° C. 1 week | 200 | MeOH/0.1 N HCl(1:1) | — | 102 |
| 4° C. 1 week | 10 | 0.05 M phosphate pH 6 | 104 | — |
| RT 1 week | 10 | 0.05 M phosphate ph 6 | 96 | 99.6 |
| 60° C. 1 week | 10 | 0.05 M phosphate pH 6 | 5 | 104 |
| 4° C. 1 week | 10 | 0.05 M phosphate pH 7 | 96 | 97.7 |
| RT 1 week | 10 | 0.05 M phosphate pH 7 | 87 | 105.8 |
| 60° C. 1 week | 10 | 0.05 M phosphate pH 7 | 0 | 97.7 |
| 4° C. 1 week | 10 | 0.05 M phosphate pH 8 | 80 | 93.2 |
| RT 1 week | 10 | 0.05 M phosphate pH 8 | 62 | 85.9 |
| 60° C. 1 week | 10 | 0.05 M phosphate pH 8 | 0 | 91.9 |
| 60° C. 2 weeks | 10 | 0.05 M phosphate pH 6 | — | 101 |
| 60° C. 1 week + RT 1 week | 10 | 0.05 M phosphate pH 6 | — | 96 |
| 60° C. 2 weeks | 10 | 0.05 M phosphate pH 7 | — | 100 |
| 60° C. 1 week + RT 1 week | 10 | 0.055 M phosphate pH 7 | — | 84 |
| 60° C. 2 weeks | 10 | 0.05 M phosphate pH 8 | — | 104 |
| 60° C. 1 week + RT 1 week | 10 | 0.05 M phosphate pH 8 | — | 37 |

*Aqueous media unless stated otherwise.
**All samples except those stored at RT were protected from light.

We claim:

1. A process for stabilizing procaterol comprising the steps of:

(1) contacting at least one of procaterol or a pharmaceutically acceptable salt thereof with a suitable reagent to produce a derivative which conforms to the formula:

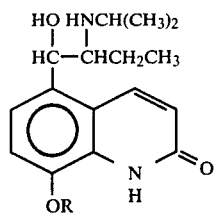

wherein R is a $C_{2-10}$ alkyl aralkyl, alkaryl, or acyl group; and (2) recovering that derivative.

2. The process of claim 1 wherein the derivative is 8-ethoxyprocaterol.

3. A pharmaceutical composition containing at least one derivative produced in accordance with the process of claim 2.

4. A pharmaceutical composition containing at least one derivative produced in accordance with the process of claim 1.

* * * * *